(12) United States Patent
Manak et al.

(10) Patent No.: US 9,055,913 B2
(45) Date of Patent: Jun. 16, 2015

(54) SYSTEM AND METHOD FOR ORIENTING AN X-RAY DETECTOR (75) Inventors: Joseph John Manak, Albany, NY (US); Bernhard Erich Hermann Claus, Niskayuna, NY (US); Jens Rittscher, Ballston Lake, NY (US); Hao Lai, Niskayuna, NY (US); Jeffrey Wayne Eberhard, Albany, NY (US); Kedar Bhalchandra Khare, Niskayuna, NY (US); Cyril Riddell, Issy-les-Moulineaux (FR); Yves Lucien Trousset, Palaiseau (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 22 days.

(21) Appl. No.: 13/098,173

(22) Filed: Apr. 29, 2011

(65) Prior Publication Data

US 2012/0275563 A1    Nov. 1, 2012

(51) Int. Cl.
*H01J 31/49* (2006.01)
*A61B 6/00* (2006.01)
*A61B 6/02* (2006.01)

(52) U.S. Cl.
CPC .............. *A61B 6/4452* (2013.01); *A61B 6/00* (2013.01); *A61B 6/027* (2013.01)

(58) Field of Classification Search
CPC .......... A61B 6/4452; A61B 6/00; A61B 6/027
USPC ..................................... 378/189, 193–203, 62
See application file for complete search history.

(56) References Cited

U.S. PATENT DOCUMENTS

| 4,922,512 | A * | 5/1990 | Lajus et al. | 378/197 |
|---|---|---|---|---|
| 6,428,206 | B1 * | 8/2002 | Watanabe | 378/197 |
| 7,054,409 | B2 | 5/2006 | Ross et al. | |
| 7,236,572 | B2 | 6/2007 | Maschke | |
| 7,592,597 | B2 | 9/2009 | Hefetz et al. | |
| 2009/0010394 | A1 * | 1/2009 | Watanabe | 378/145 |
| 2009/0024025 | A1 * | 1/2009 | Maschke et al. | 600/425 |
| 2011/0033024 | A1 | 2/2011 | Dafni et al. | |

FOREIGN PATENT DOCUMENTS

| JP | 2006263225 A | 10/2006 |
|---|---|---|
| JP | 2011019801 A | 2/2011 |

OTHER PUBLICATIONS

Search Report and Written Opinion from corresponding EP Application No. 12165648.2-1265 dated Jul. 17, 2012.

* cited by examiner

*Primary Examiner* — Hoon Song
(74) *Attorney, Agent, or Firm* — Fletcher Yoder, P.C.

(57) ABSTRACT

The subject matter disclosed herein relates to X-ray imaging systems, and more specifically to digital X-ray imaging systems. In one embodiment, an imaging system includes an X-ray source configured to emit X-rays. The imaging system also includes an X-ray detector configured to detect the emitted X-rays and produce a corresponding electrical signal. The imaging system also includes a gantry configured to at least partially revolve the X-ray source and the X-ray detector about a primary rotational axis. The X-ray detector is coupled to the gantry so that a diagonal of the X-ray detector is oriented substantially perpendicular to the primary rotational axis.

9 Claims, 5 Drawing Sheets

SYSTEM AND METHOD FOR ORIENTING AN X-RAY DETECTOR

BACKGROUND

The subject matter disclosed herein relates to X-ray imaging systems, and more specifically to digital X-ray imaging systems.

Patient imaging systems are commonly used by medical professionals to examine and diagnose patients. Generally speaking, when performing an X-ray exam, a patient is typically located between an X-ray source and detector that are designed to collect X-ray attenuation data as the patient is imaged. The various paths that X-rays traverse from the X-ray source, through the patient, and to the X-ray detector define a field of view for each projection acquired. However, since the detector is often an expensive component to manufacture, where the cost increases with increasing detector size, a detector may be utilized that is smaller than the patient being imaged. Additionally, the detector may be placed at a distance away from the patient to allow the source and detector sufficient space to move with respect to the patient. This spacing also serves to limit the inadvertent detection of X-rays that have been scattered by the patient's tissue.

Thus, in view of the limited size of the detector, the field of view for each projection may not completely span the patient's dimensions that need to be imaged, omitting information near the edges of the field of view. As a result, while projection data gleaned from patient tissue located near the center of the field of view may be relatively complete, the incompleteness of the projection data near the edges of the field of view may produce artifacts and distortions in the resulting images as a consequence of the image reconstruction algorithm attempting to properly represent the patient's tissue from an incomplete set of projection data. For example, during a patient examination involving imaging of a patient's chest cavity, portions of the patient's arm may be within the field of view for some projections and not others, providing the image reconstruction algorithm with incomplete or ambiguous projection data regarding the location and density of the patient's arm. As a result, the image reconstruction algorithm must resolve this ambiguity and determine how to incorporate the incomplete projection data into the remainder of the patient's projection data. This can result in an image with, for example, streaking artifacts near the center and/or ringing artifacts near the edges of the resulting images.

Therefore, it would be beneficial to optimize the field of view during patient imaging in order to provide the image reconstruction algorithm with the most complete projection data set possible.

BRIEF DESCRIPTION

In one embodiment, an imaging system is presented. The imaging system includes an X-ray source configured to emit X-rays. The imaging system also includes an X-ray detector configured to detect the emitted X-rays and produce a corresponding electrical signal. The imaging system also includes a gantry configured to at least partially revolve the X-ray source and the X-ray detector about a primary rotational axis. The X-ray detector is coupled to the gantry so that a diagonal of the X-ray detector is oriented substantially perpendicular to the primary rotational axis.

In another embodiment, an imaging system is presented. The imaging system includes an X-ray source configured to emit X-rays. The system also includes an X-ray detector configured to detect the emitted X-rays and produce a corresponding electrical signal. The system also includes a gantry configured to at least partially revolve the X-ray source and the X-ray detector about a primary rotational axis. The X-ray detector is rotatably coupled to the gantry and is operable to partially rotate about a secondary rotational axis during patient imaging.

In another embodiment, a method for acquiring X-ray data is presented. The method includes rotating an X-ray detector about an axis of rotation extending through the X-ray detector so that a diagonal of the X-ray detector is substantially perpendicular to an axis of revolution during at least a portion of X-ray data acquisition. The method also includes revolving a gantry, an X-ray source, and the X-ray detector about the axis of revolution during at least a portion of X-ray data acquisition. The method also includes reading X-ray image data from the X-ray detector.

BRIEF DESCRIPTION OF THE DRAWINGS

These and other features, aspects, and advantages of the present system will become better understood when the following detailed description is read with reference to the accompanying drawings in which like characters represent like parts throughout the drawings, wherein.

DETAILED DESCRIPTION

While the present discussion may be directed toward an X-ray imaging system, it should be appreciated that the present implementations may be beneficial to any imaging system where the orientation of a detector may be adjusted to improve the field of view of the system. Furthermore, while the disclosed embodiments may be directed toward X-ray patient imaging system, it should be appreciated that improving the field of view, as discussed herein, may be beneficial to other X-ray imaging systems, such as imaging system for industrial or security applications.

For the reasons set forth above, it would be beneficial to optimize the field of view for patient imaging in certain dimensions and for certain views. The present disclosure accomplishes this by rotating the orientation of the X-ray detector prior to and/or during the exam in order to optimize the field of view in certain dimensions for some or all of the acquired projections. More specifically, the detector may be rotated so that the dimension of the detector having the greatest length is aligned with a particular dimension (e.g., the height or the width) of the patient or with a particular axis (e.g., the Z-axis) of the imaging system during some or all of the image data acquisition process. By optimizing the field of view in the dimension of interest for some or all of the projections, a more complete set of projection data may be obtained during the patient exam, resulting in fewer ambiguities for the image reconstruction algorithm to resolve and final images with fewer artifacts (e.g., streaking or ringing artifacts). Optimizing the field of view relative to a particular dimension of interest may also reduce the number of radiation exposures required to examine a particular region of a patient and/or lower the probability of having to repeat the exam due to image artifacts or distortions. This may reduce the amount of radiation to which the patient is exposed in order to obtain suitable images.

Additionally, the present technique may be applied to improve the effectiveness of common detectors. For example, by making effective use of the dimensions of the detector to optimize the field of view in certain dimensions during imaging, patients of dramatically different sizes (e.g., from a large adult to a neonate) may be properly imaged without the need for specialized detectors. Further, this technique may be applied through the modification of existing X-ray imaging systems to improve the effectiveness of the original detector. Therefore, the present technique addresses the aforementioned problem in a cost-effective manner.

Generally speaking, in certain embodiments disclosed herein the detector may be oriented to provide an enhanced or optimized field of view and non-rotatably affixed to the gantry during manufacturing of the X-ray imaging system to provide the advantages described above. In another embodiment, the detector may be rotatably attached to a gantry or C-arm of an X-ray imaging system, and the detector may be rotated prior to and/or during the exam. In one such embodiment, the detector may be oriented and/or rotated using a controlled motorized system.

Figure 1:
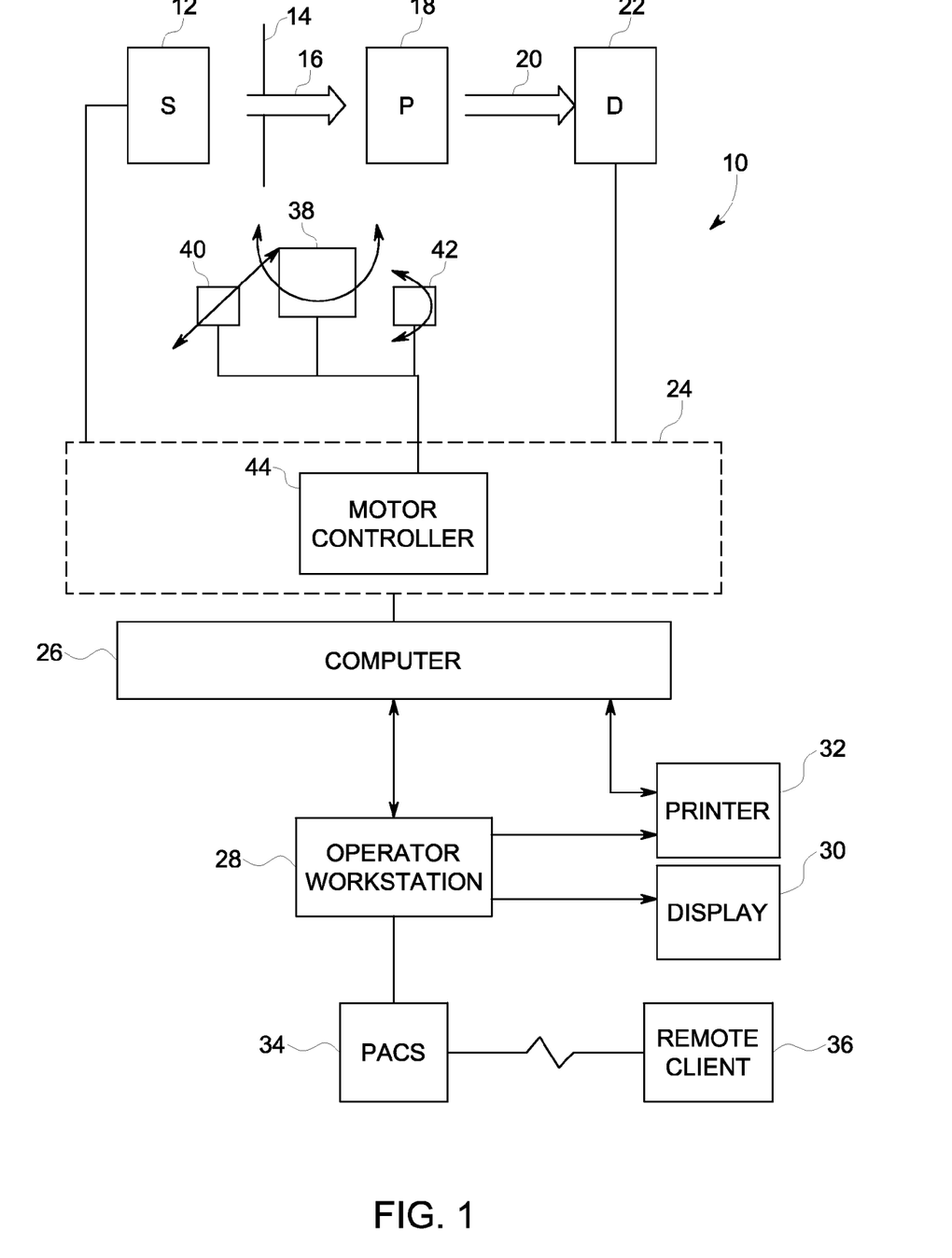
FIG. 1 is a diagrammatical view illustrating an embodiment of patient imaging system, in accordance with aspects of the present disclosure.

For example, FIG. 1 illustrates diagrammatically an imaging system 10 for acquiring and processing image data. In the illustrated embodiment, system 10 is an X-ray imaging system designed to acquire image data at a variety of radial views with respect to the patient. In the embodiment illustrated in FIG. 1, imaging system 10 includes a radiation source 12 positioned adjacent to a collimator 14. In such an embodiment, the radiation source 12 may be, for example, an X-ray tube or solid-state X-ray source. The collimator 14 permits a stream of X-ray radiation 16 to pass into a region in which a subject (e.g., patient 18) is positioned. A portion of the radiation 20 passes through or around the subject and subsequently impacts a detector 22. The detector 22 produces electrical signals that represent the intensity of the incident X-ray beam. These signals may be acquired and processed to reconstruct an image of the features within the subject.

In general, system controller 24 commands operation of the imaging system to execute examination protocols and to process acquired data. For example, the radiation source 12 is controlled by a system controller 24 that furnishes both power and control signals for the X-ray examination. Moreover, detector 22 is coupled to the system controller 24, which commands acquisition of the signals generated in the detector 22. The system controller 24 may also execute various signal processing and filtration functions, such as for initial adjustment of dynamic ranges, noise filtering, and so forth. The system controller 24 may also include signal processing circuitry, typically based upon a general purpose or application-specific circuitry, interface circuits, and so forth. The system controller 24 may also include associated memory circuitry for storing configuration parameters, image data, and/or programs and routines to be executed.

A computer 26 may also be coupled to the system controller 24. The data collected by the system controller 24 may be transmitted to the computer 26 and stored, for example, in memory for further processing. Also the computer 26 may be configured to receive commands and scanning parameters from an operator via an operator workstation 28, typically equipped with a keyboard and other input devices. An operator may control the system 10 via the input devices. A display 30 coupled to the operator workstation 28 may be utilized to observe the reconstructed image and to control imaging. Additionally, the scanned image may also be printed on to a printer 32 which may be coupled to the computer 26 and the operator workstation 28. Further, the operator workstation 28 may also be coupled to a picture archiving and communications system (PACS) 34. It should be noted that PACS 34 may be coupled to a remote system 36, radiology department information system (RIS), hospital information system (HIS) or to an internal or external network, so that others at different locations may gain access to the image and to the image data. It should be further noted that the computer 26 and operator workstation 28 may be coupled to other output devices that may include standard or special purpose computer monitors and associated processing circuitry. One or more operator workstations 28 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

In the embodiment illustrated in FIG. 1, system controller 24 may also control the positioning of the source 12, the patient 18, and/or the detector 22 using the gantry (or C-arm) rotational subsystem 38, linear positioning subsystem 40, and detector rotational subsystem 42. For example, the system controller 24 may include a motor controller 44 that is coupled to the gantry rotational subsystem 38, the linear positioning subsystem 40, and/or the detector rotational subsystem 42 in order to supply these subsystems with control signals. Each subsystem may include one or more of motors, transmissions, actuators, sensors, etc. to accomplish the desired movement and positioning control.

The gantry rotational subsystem 38 enables the X-ray source 12, collimator 14 and the detector 22 to partially revolve (e.g., 90°, 180°, 360°, etc.) around the patient 18 about a primary rotational axis (i.e. the Z-axis, or axis of revolution). The linear positioning subsystem 40 enables the patient 18, or more specifically a patient table, to be linearly displaced with respect to the source 12 and detector 22. Thus, the patient table may be linearly moved (i.e. along the Z-axis) within the gantry to generate images of particular areas of the patient 18. The detector rotational subsystem 42 enables the detector to rotate about a second rotational axis, perpendicular to the primary rotational axis, as will be discussed in greater detail below. By using the combination of these three subsystems, the source, patient, and detector may each be positioned and oriented so as to provide the best field of view for the portion of the patient being imaged. In certain embodiments, the detector rotational subsystem 42 may not be present, and the detector 22 may instead be fixed at the desired angle or may be rotated by hand (i.e. manually) to the desired angle prior to image acquisition.

Figure 2:
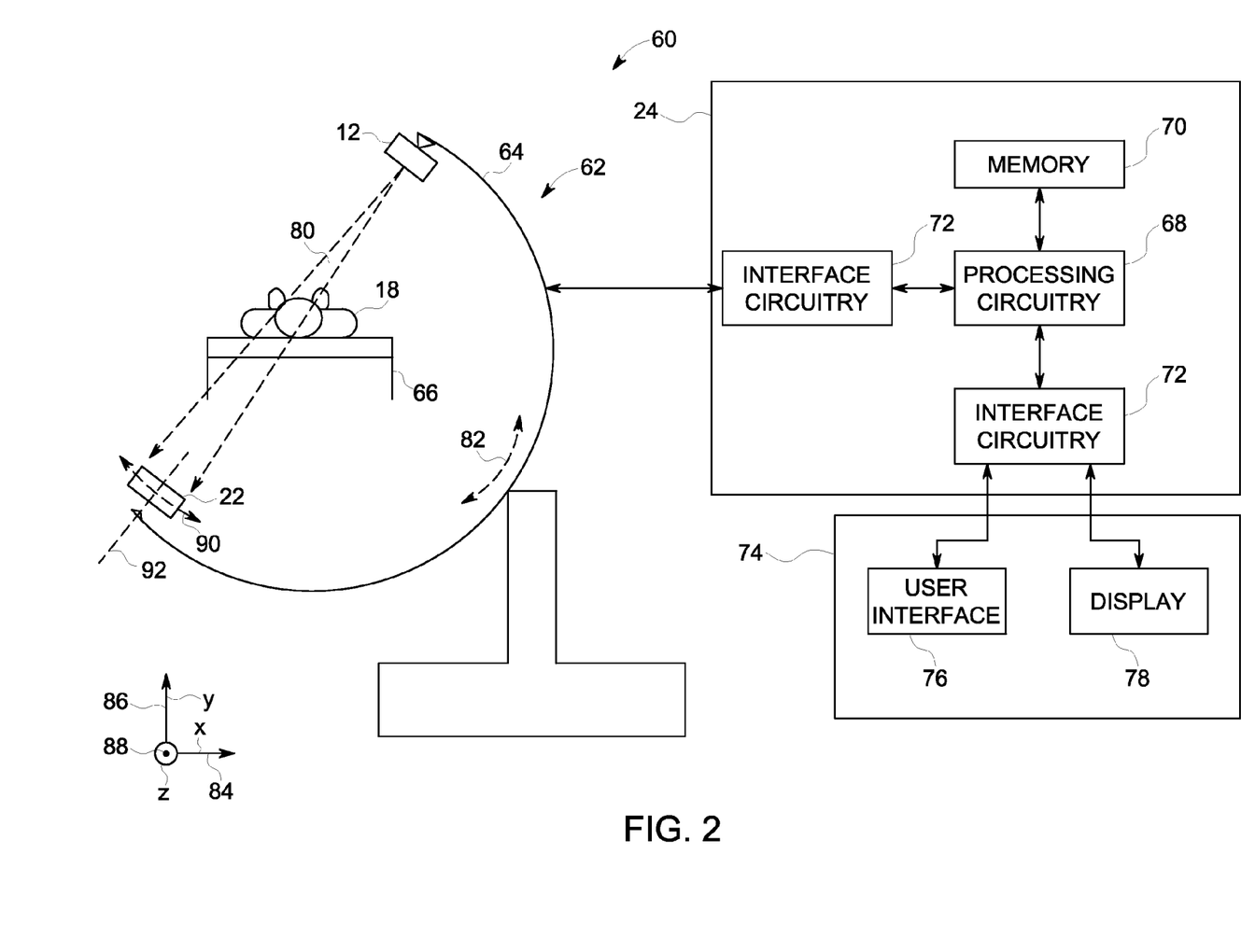
FIG. 2 is a diagrammatical view illustrating an embodiment of a patient imaging system and demonstrating the relative motion of the imaging subsystem during patient imaging, in accordance with aspects of the present disclosure.

As described above, the gantry rotational subsystem 38, the linear positioning subsystem 40, and the detector rotational subsystem 42 may cooperate to properly position the source 12, patient 18, and detector 22 for patient imaging. FIG. 2 illustrates an X-ray imaging system 60 depicting the potential movements of these components during a patient examination. The X-ray imaging system 60 includes an imaging subsystem 62 comprising the gantry 64, source 12, and detector 22, all located about the patient 18 lying on the patient table 66. The system also includes a system controller 24 having processing circuitry 68 and memory 70 for storing and processing of configuration parameters, imaging routines, image data, etc. The system controller 24 may also include interface circuitry 72 to couple to a user workstation 74. The user workstation 74 may include a user interface 76 and a display 78, to allow, for example, the input of data and parameters by a user and/or to allow the display of raw or processed image data to the user. The system controller 24 may also include interface circuitry 72 that allows the system controller 24 to be coupled to and control the imaging subsystem 62. More specifically, the system controller 24 may provide control signals to position and move the source 12, the detector 22, and the patient 18 for X-ray imaging, as will be described in greater detail below.

As mentioned above, a field of view is defined by the various paths that emitted X-rays travel from the source, through or around the patient's tissue, and to the detector. FIG. 2 illustrates one dimension of a field of view 80 for the imaging subsystem 62. As depicted, the field of view 80 extends from the source 12 to the detector 22, intersecting a portion of the patient 18 on the patient table 66; however, the field of view 80 may not encompass the entire width (e.g. the outer edges of the arms or skin lines) of the patient.

By transmitting control signals to the imaging subsystem 62, the system controller 24 may precisely control the positioning of all of the components of the imaging subsystem 62. For example, the system controller 24 may send control signals to the gantry to have it revolve 82 the source 12 and detector 22 about the Z-axis 88 (i.e. within the plane defined by the X-axis 84 and Y-axis 86) before or during patient imaging. The system controller 24 may also send control signals to the patient table 66 to cause it to move linearly (i.e. backwards or forwards along the Z-axis 88) and position the portion of the patient 18 anatomy to be imaged within the field of view 80. In one embodiment, the linear displacement of the patient table 66 along the Z-axis 88 may occur during patient imaging (e.g., helical CT imaging). Additionally, the system controller may send a control signal to the detector to cause the detector 22 to rotate 90 within the plane defined by the X-axis 84 and the Z-axis 88, about a rotational axis 92 substantially perpendicular to the Z-axis 88. This rotation 90 may occur before or during patient imaging in order to orient the detector so that the field of view may be optimized relative to one or more dimensions of the patient.

Generally speaking, FIGS. 3-10 illustrate embodiments where the field of view for a substantially square-shaped detector may be optimized by orienting or rotating the detector 22 relative to the patient. Specifically, FIGS. 3-6 depict a radiation source 12, a patient 18 lying on a patient table 66 positioned below the radiation source 12, and a radiation detector 22 positioned below the patient table 66 (i.e. a vertical arrangement). FIGS. 7-10 depict the radiation source 12 and the radiation detector 22 disposed opposite one another about the sides of the patient 18 lying on the patient table 66 (i.e. a horizontal arrangement). It should be appreciated that while an exemplary square shaped detector 22 is illustrated and discussed in reference to these figures, other embodiments may employ detectors having different geometries, such as triangular, rectangular, hexangular, octagonal, or any other polygon shape. Additionally, while vertical and horizontal arrangements for the source 12, patient 18, and detector 22 are specifically illustrated and discussed for simplicity, it should be appreciated that other source 12 and detector 22 arrangements (i.e. views) with respect to the patient 18 may benefit from the disclosed rotation of the detector 22, as discussed herein.

Figure 3:
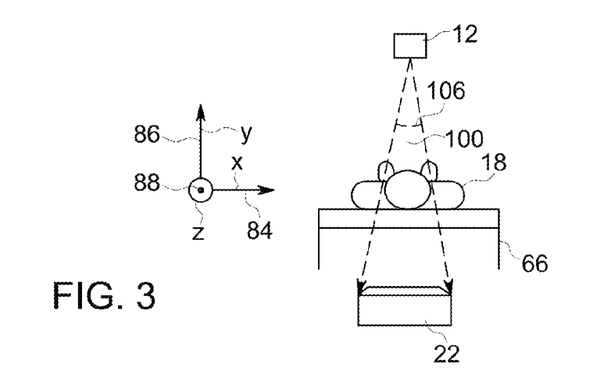
FIG. 3 illustrates an embodiment of a patient imaging system in a vertical arrangement having a field of view corresponding to a first detector orientation, in accordance with aspects of the present disclosure.
Figure 4:
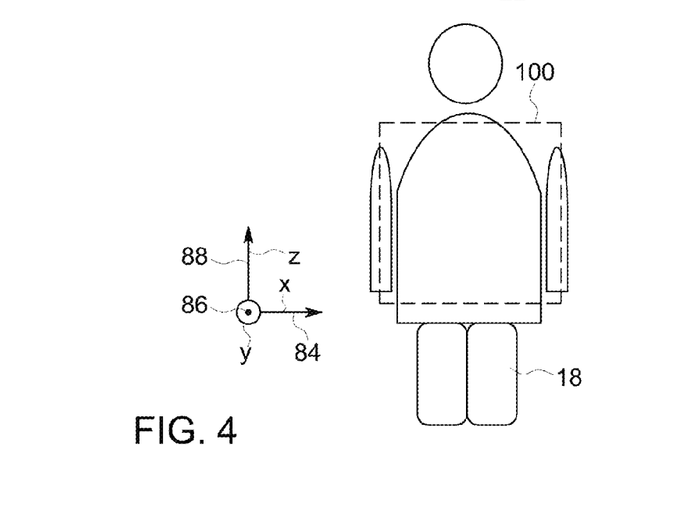
FIG. 4 is a top-down view illustrating the field of view of the system of FIG. 3.
Figure 5:
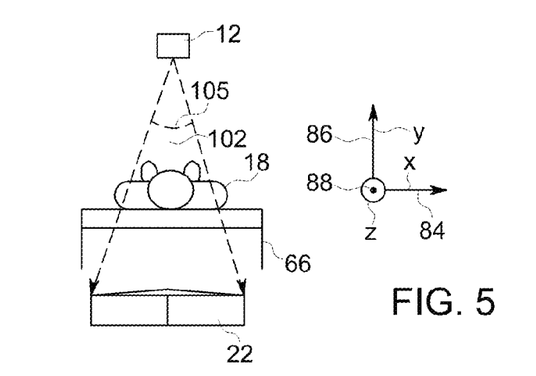
FIG. 5 illustrates an embodiment of a patient imaging system in a vertical arrangement having a field of view corresponding to a second detector orientation, in accordance with aspects of the present disclosure.
Figure 6:
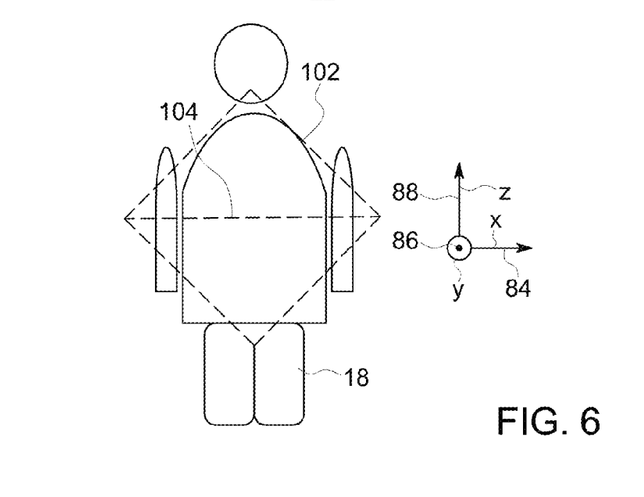
FIG. 6 is a top-down view illustrating the field of view of the system of FIG. 5.

Turning now to the figures, FIG. 3 and FIG. 5 illustrate embodiments where a radiation source 12, a patient 18 lying on a patient table 66, and a radiation detector 22 are in a vertical arrangement. In both depictions, the field of view (100 for FIGS. 3 and 102 for FIG. 5) extends from the radiation source 12 to the radiation detector 22. FIG. 4 illustrates a top-down perspective of the field of view 100 depicted in FIG. 3, while FIG. 6 illustrates a top-down perspective of the field of view 102 depicted in FIG. 5. The field of view 100 illustrated in FIGS. 3-4 is oriented such that two sides of the square detector are substantially parallel to the length of the patient 18 (i.e. the Z-axis 88), while the field of view illustrated in FIGS. 5-6 is oriented such that one of the diagonals 104 of the square-shaped detector 22 is substantially perpendicular to the length of the patient (i.e. the Z-axis 88). That is, the principle difference between FIGS. 3-4 and FIGS. 5-6 is that the detector 22 has been rotated approximately ⅛ of a full revolution (i.e. approximately 45°) about the Y-axis 86.

In comparing the figures, the differing orientation of the detector 22 results in the field of view 102 in FIG. 5 having a wider angle 105 in the X and Z directions than the angle 106 of the field of view 100 defined in FIG. 3. Accordingly, FIG. 6 demonstrates a field of view 102 that encompasses a greater portion of the patient 18 along the X-axis 84 and the Z axis 88 compared to FIG. 4. Therefore, a projection acquired from the field of view 102 defined in FIGS. 5-6 may yield more information regarding patient tissue located along the X-axis 84 and Z-axis 88 compared to a projection acquired in the field of view 100 defined in FIGS. 3-4.

For example, the substantially square-shaped detectors 22 illustrated in FIG. 3 and FIG. 5 may have a height and width of length N. Rotating the square detector ⅛ of a full revolution (i.e. 45°) about the Y-axis 86, as illustrated in FIGS. 5-6, provides a diamond-shaped field of view 102 having a height and width (i.e. diagonals of length) of N multiplied by the square root of 2. This represents approximately a 40% increase in the field of view 102 along the diagonals (e.g., diagonal 104) of the diamond-shaped field of view 102 compared to the square-shaped field of view 100. As such, the field of view 100 of FIG. 3 does not include the outer edges (i.e. skin lines) of the arms of the patient 18, while the field of view 102 of FIG. 6 does include these outer edges. Accordingly, the field of view 102 may allow the image reconstruction algorithm to produce more accurate images having fewer artifacts by providing the algorithm with projection data having more complete information (i.e. less ambiguity) regarding the outer edges the patient.

Figure 7:
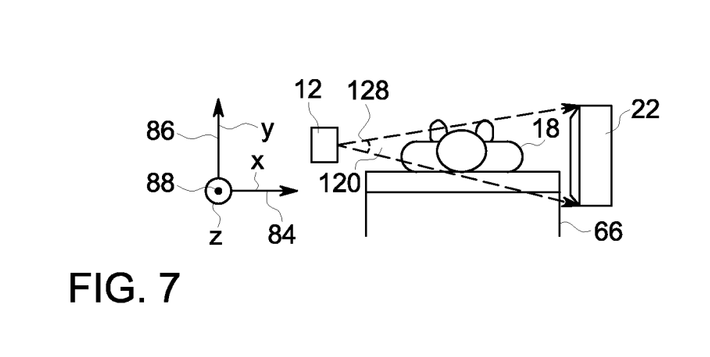
FIG. 7 illustrates an embodiment of a patient imaging system in a horizontal arrangement having a field of view corresponding to a first detector orientation, in accordance with aspects of the present disclosure.
Figure 8:
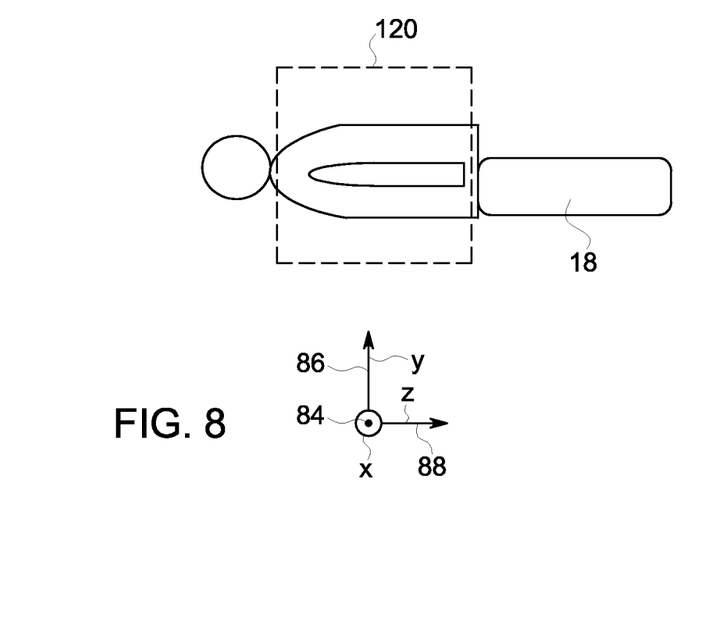
FIG. 8 is a side-view illustrating the field of view of the system of FIG. 7.
Figure 9:
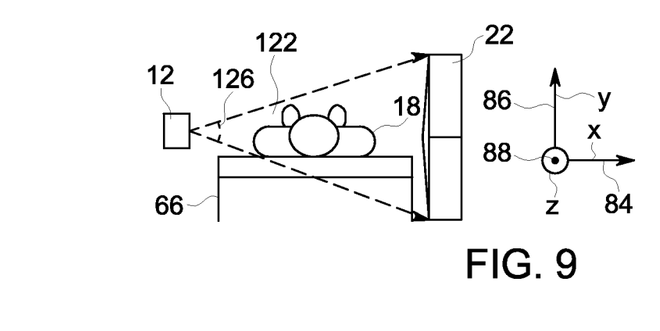
FIG. 9 illustrates an embodiment of a patient imaging system in a horizontal arrangement having a field of view corresponding to a second detector orientation, in accordance with aspects of the present disclosure.
Figure 10:
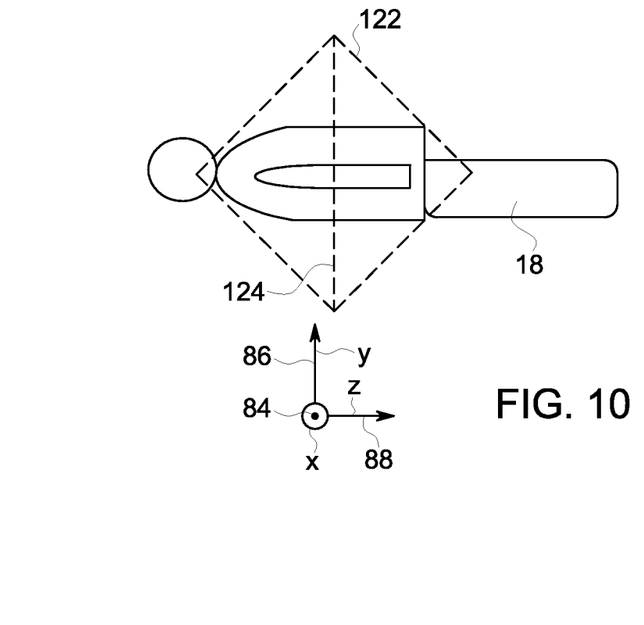
FIG. 10 is a side-view illustrating the field of view of the system of FIG. 9.
Figure 11:
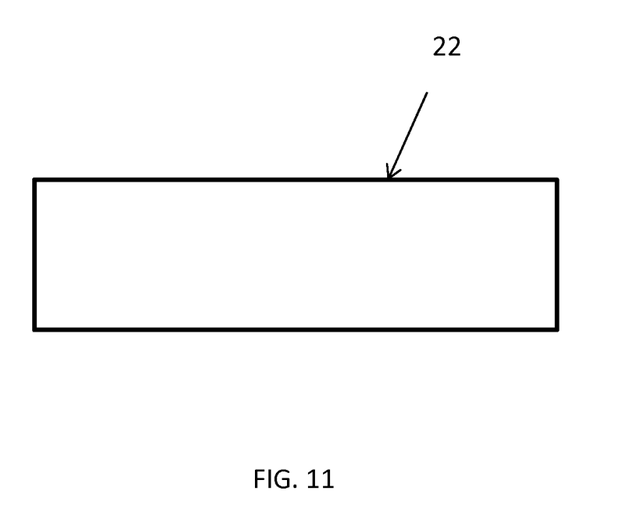
FIG. 11 illustrates a rectangular X-ray detector according to an embodiment of the invention.

Additionally, as the source and detector are revolved about the patient and the various projections are collected, the diamond-shaped field of view 102 depicted in FIG. 6 may continue to ensure that a greater degree of edge data of the patient is collected for each projection. For example, turning to FIGS. 7 and 9, a horizontal arrangement of the radiation source 12, the patient 18 lying on the patient table 66, and the radiation detector 22 is presented. For both illustrations, the field of view (120 for FIGS. 7 and 122 for FIG. 9) is depicted extending from the source 12 to the detector 22. FIG. 8 illustrates a side-view perspective of the field of view 120 depicted in FIG. 7, while FIG. 10 illustrates a side-view perspective of the field of view 122 depicted in FIG. 9. The field of view 120 illustrated in FIGS. 7-8 is oriented such that two sides of the square detector 22 are substantially parallel to the length of the patient 18 (i.e. the Z-axis 88), while the field of view 122 illustrated in FIGS. 9-10 is oriented such that one of the diagonals 124 of the square detector is substantially perpendicular to the length of the patient (i.e. the Z-axis 88). That is, a difference between FIGS. 7-8 and FIGS. 9-10 is that the detector 22 has been rotated approximately ⅛ of a full revolution (i.e. approximately 45°) about the X-axis 84.

In comparing the figures, the differing orientation of the detector 22 results in the field of view 122 in FIG. 9 having a wider angle 126 in the X and Z directions than the angle 128 of the field of view 120 defined in FIG. 7. Accordingly, FIG. 10 demonstrates a field of view 122 that encompasses a greater portion of the patient 18 along the Y-axis 86 and the Z-axis 88 compared to FIG. 8. Therefore, a projection acquired from the field of view defined in FIGS. 9-10 may yield projection data with more information regarding patient tissue located along the Y-axis 86 and Z-axis 88 compared to a projection acquired from the field of view defined in FIGS. 7-8.

In an example similar to the one provided above, the illustrated square-shaped detectors 22 may have a height and width of length N. Rotating the square detector ⅛ of a full revolution (i.e. 45°) about the X-axis 84, as illustrated in FIGS. 9-10, provides a diamond-shaped field of view 122 having a height and width (i.e. diagonals of length) of N multiplied by the square root of 2. Here again, this represents as much as a 40% increase in the field of view 122 along the diagonals (e.g., diagonal 124) of the diamond-shaped field of view 122 compared to the square-shaped field of view 120. As such, the field of view 122 may include the neck or the legs of the patient while the field of view 120 may not. Accordingly, the field of view 122 may allow the image reconstruction algorithm to produce more accurate images having fewer artifacts by providing the algorithm with projection data having more complete information (i.e. less ambiguity) regarding the outer edges the patient.

As previously mentioned, some embodiments of the present technique include a detector 22 that is fixed to gantry 64 and oriented with the longest dimension of the detector 22 (e.g., a diagonal of a square detector) substantially perpendicular to the Z-axis 88. In such an embodiment, when the source 12, detector 22, and patient 18 are in a vertical arrangement (such as in FIG. 5), or in a horizontal arrangement (such as in FIG. 9), or at any other angle, the detector 22 maintains its orientation relative to the Z-axis 88. However, for embodiments that include a detector 22 that is rotatably attached to the gantry 64, the detector 22 may change its orientation throughout patient imaging. For example, during patient imaging, the source 12, patient 18, and detector 22 may begin in a vertical arrangement with the detector 22 oriented such that the longest dimension of the detector (e.g., a diagonal of the square detector) is oriented substantially perpendicular to the Z-axis 88 (as in FIG. 5). Then, as the gantry 66 is revolved about the patient 18 and further projections are collected, the detector 22 may rotate such that by the time the source 12, patient 18, and detector 22 have reached a horizontal arrangement, the detector 22 may be oriented such that two sides of the detector are substantially parallel to the Z-axis 88 (as in FIG. 7). Alternatively, for example, the source 12, patient 18, and detector 22 may begin in a horizontal arrangement with the detector 22 rotated such that the longest dimension of the detector 22 (e.g., a diagonal of the square detector) is oriented substantially perpendicular to the Z-axis 88 (as in FIG. 9). Then, as the gantry is revolved about the patient 18 and further projections are collected, the detector may rotate gradually such that by the time the source 12, patient 18, and detector 22 have reached a vertical arrangement, the detector 22 may be oriented such that two sides of the detector are substantially parallel to the Z-axis 88 (as in FIG. 3). It should be appreciated that these examples offered merely by way of explanation, and that a variety of combinations of gantry rotational positions and detector rotational positions may be achieved, as discussed herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for X-ray data acquisition, the method comprising:
    revolving an X-ray source and an X-ray detector around an axis of revolution, wherein the X-ray source and the X-ray detector are coupled to a gantry; and
    rotating an X-ray detector about an axis of rotation, wherein the axis of rotation is perpendicular to a plane of the detector and perpendicular to the axis of revolution; and
    acquiring X-ray image data using the X-ray detector as the X-ray detector is revolving and rotating.

2. The method of claim 1, wherein rotating the X-ray detector about the axis of rotation comprises rotating the X-ray detector to provide a first field of view when the X-ray detector revolves into a first position about the axis of revolution.

3. The method of claim 2, wherein rotating the X-ray detector about the axis of rotation comprises rotating the X-ray detector to provide a second field of view when the X-ray detector revolves to a second position about the axis of revolution.

4. The method of claim 3, wherein the first field of view is provided when the X-ray detector is rotated so that a diagonal of the X-ray detector is substantially perpendicular to the axis of revolution, and the second field of view is provided when the X-ray detector is rotated so that the diagonal of the X-ray detector is substantially parallel to the axis of revolution.

5. The method of claim 1, wherein the first point in the revolution is where the X-ray source and X-ray detector are in a vertical arrangement with respect to the gantry, and the second point in the revolution is where the X-ray source and X-ray detector are in a horizontal arrangement with respect to the gantry.

6. A method for X-ray data acquisition, the method comprising:
- revolving, around an axis of revolution, an X-ray source and an X-ray detector coupled to a gantry, wherein a patient is disposed within the gantry such that a longest dimension of the patient is oriented along the axis of revolution;
- rotating the X-ray detector about an axis of rotation that is perpendicular to a plane of the X-ray detector, comprising:
    - rotating the X-ray detector so that a longest dimension of the X-ray detector is substantially parallel to the longest dimension of the patient at a first point during the X-ray data acquisition; and
    - rotating the X-ray detector so that the longest dimension of the X-ray detector is substantially perpendicular to the longest dimension of the patient during at a second point during the X-ray data acquisition; and
- acquiring X-ray image data using the X-ray detector as the X-ray detector is both revolving and rotating.

7. The method of claim 6, wherein rotating the X-ray detector so that the longest dimension of the X-ray detector is substantially parallel to the longest dimension of the patient at the first point during the X-ray data acquisition comprises rotating the X-ray detector to maximize a field of view relative to a length of the patient at the first point during the X-ray data acquisition.

8. The method of claim 6, wherein rotating the X-ray detector so that the longest dimension of the X-ray detector is substantially perpendicular to the longest dimension of the patient at the second point during the X-ray data acquisition comprises rotating the X-ray detector to maximize a field of view relative to a width of the patient at the second point during the X-ray data acquisition.

9. The method of claim 6, wherein the X-ray detector is configured to rotate by 45 degrees between the first position and the second position.

* * * * *

UNITED STATES PATENT AND TRADEMARK OFFICE
CERTIFICATE OF CORRECTION

| | | |
|---|---|---|
| PATENT NO. | : 9,055,913 B2 | Page 1 of 1 |
| APPLICATION NO. | : 13/098173 | |
| DATED | : June 16, 2015 | |
| INVENTOR(S) | : Manak et al. | |

It is certified that error appears in the above-identified patent and that said Letters Patent is hereby corrected as shown below:

In the specification

In Column 6, Line 25, delete "FIGS. 3" and insert -- FIG. 3 --, therefor.

In Column 7, Line 9, delete "FIGS. 7" and insert -- FIG. 7 --, therefor.

In Column 8, Line 1, delete "gantry 66" and insert -- gantry 64 --, therefor.

Signed and Sealed this
Twentieth Day of October, 2015

Michelle K. Lee
*Director of the United States Patent and Trademark Office*